United States Patent [19]

Spiegel

[11] Patent Number: 5,714,478
[45] Date of Patent: Feb. 3, 1998

[54] SPHINGOSYLPHOSPHORYLCHOLINE AS A WOUND-HEALING AGENT

[76] Inventor: Sarah Spiegel, 6343 Linway Ter., McLean, Va. 22101

[21] Appl. No.: 720,056

[22] Filed: Sep. 27, 1996

Related U.S. Application Data

[60] Provisional application No. 60/004,581, Sep. 29, 1995.
[51] Int. Cl.$^6$ ............................................. A61K 31/685
[52] U.S. Cl. .................................................. 514/77
[58] Field of Search ............................................. 514/77

[56] References Cited

U.S. PATENT DOCUMENTS 5,374,616 12/1994 Spiegel et al. ............................. 514/4

Primary Examiner—Zohreh Fay
Attorney, Agent, or Firm—Glenna Hendricks; Carol Carr

[57] ABSTRACT

It has now been found that at certain concentrations, sphingosylphosphorylcholine (SPC) in solution can be used for wound healing at concentrations of from 0.1 µM to 500 µM. It has been found that at concentrations of 2 µM to 10 µM very good results could be obtained. Compositions may be prepared using pharmaceutically acceptable carriers for topical application or for injection in or near the site of the wound.

9 Claims, No Drawings

SPHINGOSYLPHOSPHORYLCHOLINE AS A WOUND-HEALING AGENT

This application claims benefit of Provisional Patent Application 60/004,581 filed Sep. 29, 1995 and takes priority therefrom.

FIELD OF THE INVENTION

This invention relates to the use of sphingosylphosphorylcholine for wound healing.

BACKGROUND OF THE INVENTION

The sphingolipid metabolites, sphingosine, sphingosin-1-phosphate and sphingosylphosphorylcholine (SPC) are emerging as a new class of intracellular second messengers with a wide spectrum of activity in cell growth regulation and signal transduction. However, in spite of certain similarities in structure, SPC is unlike many of its congeners in several respects.

The use of sphingosylphosphorylcholine as a cellular growth factor to increase cell proliferation was disclosed in U.S. Pat. No. 5,374,616, which is incorporated herein by reference. However, that reference does not indicate that sphingosylphosphorylcholine (SPC) can be used for wound healing, a more complex process which requires cell recruitment and tissue remodeling in addition to cell proliferative properties. There are, in fact, many mitotic agents that are not useful for wound healing, including bombesin, bradykinin, insulin and lysophosphatidic acid. For example, data in the cited patent regarding insulin shows that insulin should be used in conjunction with SPC for synergistic effects when simple proliferation enhancement is desired. This combination taught in the prior art is not useful for purposes of wound healing.

Several factors are known to affect activity of sphingolipids in the body and have been indirectly implicated in disturbances of healing. For example, it is known that the level of sphingomyelins is altered in tissue after laser surgery. In pediatric patients with Gaucher's disease, one of the sphingolipidoses, bone fracture healing is impaired. The disease is characterized by erosion of the bone, osteonecrosis in the area of the fracture, and disuse osteoporosis. Acute disturbance of sphingolipid metabolism by the bite of the brown recluse spider, *Loxosceles reclusa*, often leads to persistent, healing-impaired sores in humans. Sphingomyelinase D, which degrades sphingomyelin to ceramide-1-phosphate, is the active agent in the venom.

DESCRIPTION OF THE INVENTION

It has now been found that sphingosylphosphorylcholine (SPC) in solution can be used for wound healing at concentrations of from 0.1 µM to 500 µM in solution. It has been found that at concentrations of 2 µM to 10 µM very good results could be obtained. Compositions may be prepared using pharmaceutically acceptable carriers for topical application or for injection in or near the site of the wound. Compositions for injection include sterile, distilled water, saline (including buffered saline), glucose, and so forth. For topical application, compositions useful for injection may be used. However, other carriers usually used in pharmaceuticals for topical composition may be used to deliver medicaments in forms such as gels, lotions, foams and sprays. Compositions containing SPC may be administered on solid supports, including bandages and applicators which are impregnated with the SPC. Additionally, it is possible to apply compositions such as solutions or gels containing SPC with solid, non-absorbent applicators such as plastic or glass rods. Such non-absorbent applicators may be conveniently attached to the closing means of a container which contains SPC in a carrier. SPC may also be administered in a cyclodextrin inclusion complexes as a powder or a lozenge.

When used as a wound-healing agent, the SPC is administered to the locus of the wound. It may be administered in conjunction with other active agents such as antibiotics or anti-inflammatory agents. For such applications salves, gels or lotions may be particularly useful.

SPC may also be applied as a spray to abraded skin after wound cleansing. SPC may be administered to other epithelial tissue such as the rectum or vagina in the form of suppositories, retention enemas or as douches.

The particular carriers used and the mode of administration will depend on the locus of the wound. If other active agents are present in the medicament, the carrier may be chosen on the basis of its usefulness in applying the other active agents.

The following examples are meant to illustrate the invention and are not to be considered to in any way limit the scope of the invention.

Materials and Methods

Sphingosylphosphorylcholine was obtained from Sigma Chemical Co. (St. Louis, Mo.) and was analyzed as having greater than 95% purity by thin-layer chromatography. This SPC was prepared by acid hydrolysis of bovine brain sphingomyelin, a procedure that has been reported to yield a 72:28 D-erythro/L-threo mixture with mitogenic properties identical to 2S, 3R, 4E (D-erythro) SPC. Insulin, transferrin and the cell growth media, Dulbecco's modified Eagle's medium, M199 and Waymouths were obtained from Gibbco-BRL (Gaithersburg, Md.). NIH/3T3 and BALB/3T3 fibroblast cells were obtained from the American Type Culture Collection (ATCC, Rockville, Md.). Porcine aorta endothelial cells, porcine cerebral microvessel endothelial cells (PCMVEC) and retro-virus transformed porcine cerebral microvessel endothelial cells (RVTE) were isolated and obtained as described. 5-Bromo-2'-deoxyuridine (BrdU) was purchased from Sigma. Genetically healing-impaired diabetic mice (db/db) and their normal littermates (db/+), on a C57B/KsJ phenotypic background, were from Jackson Laboratories (Bar Harbor, Maine).

Cell Proliferation Assay In Vitro: Cells at 60% to 80% confluence were seeded at a density of $5 \times 10^3$ cells/well into Falcon 96-well plates in Dulbecco's modified Eagle's medium (for NIH/3T3 and BALB/3T3) and in M199 (for PAEC, PCMVEC, and RVTE). The media were supplemented-with 10% fetal bovine serum, penicillin (100 units/ml), and streptomycin (100 µg/ml). On the day of the study, the medium was changed to Dulbecco's modified Eagle's medium/Waymouths (1:1) containing bovine serum albumin (20 µg/ml), transferrin (5 µg/ml), and insulin (2 µg/ml). The cells were exposed to the absence or presence of SPC (10 µg/ml) for 24 hours, then incubated with 0.4 µCi of [$^3$H] thymidine for another 20 hours. The fold stimulation of incorporation of [$^3$H] into trichloroacetic acid-insoluble material was calculated relative to controls. Values are the means of triplicate determinations. Standard deviations were routinely less than 10%.

Cell Proliferation Assay In vivo: BrdU (an analog of thymidine) labeling and immunostaining, a sensitive technique to identify cells in S-phase, was used to assess cell proliferation in wound tissue. Sixty-four mice (32 db/+ and 32 db/db mice) aged 8–11 weeks old were divided into four equal groups: SPC-treated or phosphate-buffered saline (PBS)-treated excisional and incisional groups. In the excisional wound groups, a small full-thickness 6 mm diameter incisional wound was made on the mid-dorsum with a sterile biopsy punch and was treated with a 10 µl dose of SPC (0.02 ηM) in PBS or PBS only once daily. The incisional wound groups were subjected to a full-thickness incision about 2 cm in length and received 15 µl/dose of 2 µM SPC (0.03 ηm) in PBS with 5 µl applied topically and 10µ administered subcutaneously to the base of the wound once daily. The corresponding controls received only PBS and were processed identically. To prevent disturbance of the wounds by licking, the animals were individually housed after creation of the wounds. The SPC-treated wounds and controls in both excisional and incisional groups were harvested from 1 db/+ mice on days 2, 3, 4 or 6 after wounding. Similarly, wounds were harvested from four, two and two db/db mice at day 4, 6 and 7 respectively after wounding. Each animal received a single intravenous injection of BrdU at a dosage of 50 mg/kg body weight 1 hours before death.

Wound area measurement: A single full-thickness 6-mm diameter excisional wound was made with a sterile biopsy punch on the mid-dorsum of each db/db mouse and left undressed. In each study, groups of five mice were treated with one of several concentration of SPC in PBS or with PBS vehicle only (control). Mouse wounds were treated with a 10 µl dose of either SPC solution o4 PBS only applied topically once daily for 15 consecutive days after injury. Scabs were gently removed on days 4, 6, 8, 10, 12, 14 and 16 post-injury to accurately visualize the wound margins and to facilitate SPC access to the wound. The wounds and a centimeter scale were photographed one hour after wounding (day 0) and on alternate days thereafter. Each photograph was processed to amplify the wound area to 50 to 100 times the original. Image analysis software supplied with the Bio-Rad MRC 500 confocal system (Bio-Rad Laboratories, Microscience, Lt., Hemel Hempstead, UK) was used for measurement of the amplified wound areas. (Mean±SD) wound areas were expressed as percent of initial wound area at day 0.

Breaking strength measurement: Linear incisions about 2 cm in length were made on the dorsal aspect of the db/db mice as described above. Thirteen mice (total of three experiments) each received 15 µl of 2 µM SPC in PBS once daily for 12 days (5 µl applied topically to incision margins and 10 µl injected subcutaneously into the base of the incision). The mice were sacrificed at day 17 (8 mice) or day 27 (5 mice) post-injury. A similar group was used as a control using PBS vehicle only. The wound strip was excised from the dorsal skin and cut into an 8-mm wide strip using a template. Breaking strength was measured immediately after excision using a custom-made tensiometer. Tension was applied at a constant rate of 1 cm/min using a 1.0-Kg force transducer. Statistical significance of responses were evaluated using a one-way analysis of variance.

Tissue processing and quantitative assessment: To visualize BrdU incorporation and neoangiogenesis, immunostaining was performed on 5 µm thick tissue sections using monoclonal antibodies against BrdU (Sigma) or factor VIII-related antigen (Zymed Laboratories, Inc., South San Francisco, Calif.) according to the procedures provided by the manufacturer. Skin samples harvested from incision wounds at day 17 after wounding were fixed in 10% formalin, embedded in paraffin, and stained with Masson trichrome. Quantitative valuation of the SPC effect on wound healing was performed at an objective lens modification of 4× and 10× with a Nikon Optiphot microscope interfaced via a color camera to an image analysis system (Bio-Scan Inc., Edmonds, Wash.). The number of BrdU-labeled cells, the cross-sectional scar area, and the thickness of dermal and adipose layers were measured in wound sites. Values are the means (±SD) of two to three slides from each animal in the groups.

Results

Excisional wounds in db/db mice were treated with concentrations of SPC of from 0.5 µM to 100 µM. Initial studies established that a wide range of concentrations (0.5µ to 50 µM) were beneficial and indicated a very high rate of effectiveness that at a concentration of 2–3 µM. Measurement of the wound areas demonstrated that wounds treated with concentrations of SPC at 2.5 µM to 10 µM became smaller than control wounds and that the improvement in healing became statistically significant ($p<0.05$) by day 10 of the healing process. When the effect of 3 µM SPC was compared in all tests, a steady and statistically significant ($p<0.02$) improvement was found until the healing was essentially complete. These full-thickness lesions in mice may simulate deep dermal decubitus and diabetic ulcers in human. Such wounds frequently penetrate through the dermis and are often debrided to remove necrotic tissue prior to treatment, thereby generating a deep wound bed similar to that produced by punch biopsy in rodents. The effect of SPC on wound strength was evaluated by application to the incisional wounds in db/db mice.

Histological examination of SPC-treated wounds at day 17 after wounding revealed minimal scar contracture, a more normal complement of fat cells in the dermal layer and the subcutaneous layer.

Quantitative analysis of the quality of healing was determined by measuring cross-sectional scar area, the thickness of the dermis, and the thickness of the adipocyte layer. SPC treatment led to significantly smaller scar area and more normal adipocyte layer compared with corresponding controls, indicating an improvement of wound quality by the application of SPC. In three tests, SPC produced a consistent, but not significant, increase in skin breaking strength with improvement of 24% over controls at day 17 post-wounding and 15% over controls at day 27 after wounding.

In order to evaluate the effect of SPC earlier in the healing process, the cell proliferation in vivo was evaluated in tissue sections. SPC induced an early and profound keratinocyte proliferation and migration of epidermis to the margin of excisional and incisional wounds in both db/db and db/+ strains of mice, while tissue repair in PBS-treated controls was much slower. The SPC-treated incisional wounds of db/db mice were completely re-epithelialized at day 4 after wounding, and a large amount of granulation tissue filled the wound sites. There was a high density of BrdU-labeled cells, whereas the controls had fewer BrdU-labeled cells and a less organized wound tissue. At higher magnification, it was clear that SPC stimulated proliferation of cells in the wound margin, cells (presumably keratinocytes) at the dermal-epidermal junction, individual cells in the dermis, and cells in the dermis located in sebaceous glands and the outer root sheath of hear follicles. The tissue response to SPC stimulus in the db/+ mice was similar, but much earlier than that in db/db mice. Similar results were also seen in the SPC-treated excisional wounds. The effects of SPC on in vivo cell proliferation were quantified by image analysis. SPC treatment led to statistically significant increases ($p<0.01$) in numbers of mitotic cells, up to a 3-fold increase. In SPC-treated wounds, many endothelial cells in the walls of neo-capillaries were labeled with BrdU and could be distinguished by their flat cross-section. The intensive staining of factor VIII-related antigen and the increase in the number of neo-capillaries showed that SPC was a potent stimulator of endothelial cell proliferation and neoangiogenesis.

It was also shown that SPC stimulates cell proliferation in vitro. For comparison, the effect of SPC was also evaluated on the growth of several types of cultured cells, including 3T3 fibroblasts, primary endothelial cells and virally-transformed endothelial cells. SPC greatly stimulated DNA synthesis in all of these cells. Consistent with studies on other cells, including large vessel endothelial cells, SPC caused a concentration-dependent increase in [$^3$H]thymidine incorporation into DNA with a maximum effect at 10 µM. The stimulation of endothelial cell proliferation supported the observation in vivo and was similar in magnitude to the aggregate cellular response in vivo.

The dose-response to SPC in promoting excision wound closure indicated that not only was SPC efficacious, but also that optimal efficacy could be achieved using 2–3 µM solutions, a level consistent with the in vitro dose response for growth of fibroblasts and endothelial cells. Our results showed that SPC appeared to enhance wound closure over a wide range of concentrations. The small but consistent increase in breaking strength in the three mouse incision wound tests was also observed within this dosage range.

It is especially important that SPC effected wound healing without increase in wound dehiscence. Agents that would improve the rate of closure at the expense of wound strength are of little clinical value. For example, basic fibroblast growth factor applied to healing collateral ligaments improved angiogenesis, but decreased ligament tensile strength. Conversely, SPC increased the rate of wound closure with no deterioration of strength in the wound area. The more normalized tissue in dermis and subcutaneous layers in the incision site may contribute to the increase of breaking strength, compared with the scar tissue in controls. SPC stimulated profound granulation tissue formation, angiogenesis, and epithelial proliferation early in the wound healing process, and greatly decreased scar tissue amount while increasing the adipose component at a late stage of healing, suggesting effect of SPC on both acceleration of tissue repair and on tissue remodeling.

Although the clearly statistically significant improvement in wound healing was evident late in the healing process, a key event was the stimulation of cell proliferation in the wound early in the healing process. SPC stimulated a wide variety of skin cells types in vivo. The proliferation of cells including keratinocytes at the dermal epidermal junction, epithelial cells associated with sebaceous glands and hair follicles, vascular endothelial cells, fibroblasts in the dermis was increased. This response to SPC is similar to the cell activation that occurs during normal healing, but the stimulation results in earlier and more profound healing effects.

Because compositions containing SPC as an active agent result in less scarring of tissue during wound healing, such compositions are particularly valuable for use during and after reconstructive or cosmetic surgery. Using the compositions of the invention as sprays or topical applications after removal of the outer layer of the skin such as is practiced on patients with acne not only heals the wounds more quickly, but also results in less scarring.

Compositions containing SPC can also be used to treat patients with decubitus ulcers. A spray or mist containing SPC would be appropriate for such purposes. Since SPC is water-soluble, a water-based carrier may be used such as phosphate-buffered saline, or half-normal saline may be used. Preservatives and coloring agents may also be added.

The spray may simply be formed by an atomizer on the container, it is not necessary to use a special carrier to enhance vaporization, though use of a vehicle to enhance vaporization is not precluded. It is also possible to deliver compositions containing the active agent using a smooth solid support such as a smooth glass or plastic rod. It is also possible, for application to lesions such as decubitus ulcers, to add a colorant to the composition so that the area to which the composition has been applied may be clearly visualized. The application of SPC as a spray or mist is a preferred mans for applying to tissue that has undergone debradement, such as burns or extensive scrapping injuries.

EXAMPLE 1

To 15 ml of phosphate buffered saline is added 3 mg of sphingosylphosphorylcholine. The composition is placed in a bottle having a stopper with a smooth glass rod extending into the solution. The composition is applied to decubitus ulcers using the smooth glass rod as an applicator. The composition may also be administered as a spray from a bottle with an atomizer.

EXAMPLE 2

To a 4×4 inch bandage having a smooth surface on one side there is applied to the smooth surface 0.02 ml of the solution prepared as a 2 µM solution in PBS. The prepared bandage is then enclosed in a foil covering which is made air-tight. For application, the bandage is unwrapped and is applied smooth side down on the wound.

EXAMPLE 3

A composition is prepared for use on the skin or mucosa in the following manner:

| Ingredient | % w/w |
| --- | --- |
| SPC | 0.5% |
| propylene glycol | 13.0% |
| Phosphate buffered saline | 86.5% |

When the active agent is administered to the mucosa of the oral cavity, it may be administered as a buccal tablet or spray for use in the oral-pharyngeal cavity and the nasal cavities.

EXAMPLE 4

A composition prepared as a gel for application to the skin:

| Ingredient | % w/w |
| --- | --- |
| SPC | 0.5% |
| propylene glycol | 10.0% |
| Polyethylene glycol | 89.5% |

EXAMPLE 5

A composition prepared for administration as a suppository:

| Ingredient | % w/w |
| --- | --- |
| SPC | 0.5 mg |
| glyceryl monosterate | 1.0 Gm |
| hydrogenated coconut oil | 1.0 Gm |
| glyceryl monopalmitate | 1.0 Gm |

I claim:

1. A method of enhancing wound-healing comprising topical application or injection into or near the wound site of a composition containing a wound-healing effective amount of sphingosylphosphorylcholine to a wound or abraded tissue.

2. A method of claim 1 wherein the composition is applied as a spray.

3. A method of claim 1 wherein the composition is applied using a solid support.

4. A method of claim 3 wherein the solid support is a smooth glass or plastic rod.

5. A method of claim 1 wherein a colorant has been added to the composition.

6. A method of claim 1 wherein the composition administered is a gel.

7. A method of claim 1 wherein the composition administered is in the form of a suppository.

8. A method of claim 1 wherein the composition is injected near the wound site.

9. A method of claim 1 wherein the composition is administered in the form of a lotion or cream.

* * * * *